(12) United States Patent
Kim

(10) Patent No.: US 11,432,790 B2
(45) Date of Patent: Sep. 6, 2022

(54) MULTI-CHANNEL DIGITAL STETHOSCOPY SYSTEM

(71) Applicant: BLAUBIT CO., LTD., Seongnam-si (KR)

(72) Inventor: Euisun Kim, Seoul (KR)

(73) Assignee: BLAUBIT CO., LTD., Seongnam-si (KR)

( * ) Notice: Subject to any disclaimer, the term of this patent is extended or adjusted under 35 U.S.C. 154(b) by 432 days.

(21) Appl. No.: 16/708,577

(22) Filed: Dec. 10, 2019

(65) Prior Publication Data
US 2021/0145397 A1    May 20, 2021

(30) Foreign Application Priority Data
Nov. 18, 2019 (KR) ........................ 10-2019-0147331

(51) Int. Cl.
| | | |
|---|---|---|
| A61B 7/00 | (2006.01) | |
| A61B 7/04 | (2006.01) | |
| A61B 5/00 | (2006.01) | |
| H04R 3/04 | (2006.01) | |
| G10L 21/0232 | (2013.01) | |
| H04S 3/00 | (2006.01) | |
| H04R 1/46 | (2006.01) | |

(52) U.S. Cl.
CPC ............ *A61B 7/003* (2013.01); *A61B 5/0002* (2013.01); *A61B 5/6801* (2013.01); *A61B 5/7225* (2013.01); *A61B 7/04* (2013.01); *G10L 21/0232* (2013.01); *H04R 1/46* (2013.01); *H04R 3/04* (2013.01); *H04S 3/008* (2013.01); *H04R 2420/07* (2013.01); *H04S 2400/01* (2013.01); *H04S 2400/15* (2013.01)

(58) Field of Classification Search
CPC ....... A61B 7/003; A61B 5/002; A61B 5/6801; A61B 5/7225; A61B 7/04; G10L 21/0232; H04R 1/46; H04R 3/04; H04R 2420/07; H04S 3/008; H04S 2400/01; H04S 2400/15
See application file for complete search history.

(56) References Cited

U.S. PATENT DOCUMENTS

2021/0386394 A1\* 12/2021 Hsu ..................... A61B 5/6843

\* cited by examiner

*Primary Examiner* — Andrew L Sniezek
(74) *Attorney, Agent, or Firm* — NSIP Law

(57) ABSTRACT

Disclosed is a multi-channel digital stethoscopy system. The present invention can provide accurate and detailed medical examination information by separating and filtering stethoscopy sounds received from a plurality of transmission units by frequency in a single reception terminal, dividing the filtered stethoscopy sounds into cardiac sounds and lung sounds, and then outputting the same.

6 Claims, 4 Drawing Sheets

PRIOR ART

MULTI-CHANNEL DIGITAL STETHOSCOPY SYSTEM

CROSS-REFERENCE TO RELATED APPLICATIONS

This application claims the benefit under 35 USC § 119(a) of Korean Patent Application No. 10-2019-0147331 filed on Nov. 18, 2019 in the Korean Intellectual Property Office, the entire disclosure of which is incorporated herein by reference for all purposes.

BACKGROUND OF THE INVENTION

1. Field of the Invention

The present invention relates to a multi-channel digital stethoscopy system and, more particularly, to a multi-channel digital stethoscopy system for separating and filtering stethoscopy sounds received from a plurality of transmission units by frequency in a single reception terminal, dividing the filtered stethoscopy sounds into cardiac sounds and lung sounds, and then outputting the same.

2. Description of the Prior Art

When a patient undergoes an operation or is placed under anesthesia during a procedure at a medical institution, the medical staff must listen to a patients cardiac sound or lung sound to frequently check whether or not the health condition of the patient suddenly changes due to the operation or anesthesia.

At this time, the listening of the patients cardiac sound or lung sound is generally performed by an existing stethoscope. When using an existing stethoscope, only one medical staff who uses the stethoscope is able to check the health condition of the patient, and the medical staff must keep close to the patient.

Recently, a technique for transmitting a stethoscopy sound converted into a digital signal to an external device has been proposed.

Korean Patent Laid-Open Publication No. 10-2009-0070294 titled "Multi-vital sign wireless monitoring system" discloses a technique for transmitting a stethoscopy sound signal converted into a digital signal to a computer or other devices, thereby recovering the same.

FIG. 1 is a block diagram illustrating a digital stethoscopy system according to the prior art. The stethoscopy system includes a transmission unit 10 for receiving a cardiac sound or a lung sound of a patient, converting the same into a digital signal, and transmitting the converted stethoscopy sound and a reception unit 20 for receiving and outputting the stethoscopy sound transmitted from the transmission unit 10.

The transmission unit 10 is configured to include an sound input unit 11 for receiving a cardiac sound or a lung sound, an amplifier 12 for amplifying the received cardiac sound or lung sound, a filter 13 for filtering a noise signal, and an analog-to-digital converter (ADC) 14 for converting an analog signal into a digital signal, and a wireless communication unit 15 for transmitting the digital signal using short-range communication.

In addition, the receiver 20 includes a wireless communication unit 21 for receiving the digital signal transmitted from the transmission unit 10 and a sound output unit 22 for converting the digital signal into a sound signal and outputting the same.

However, the cardiac sound or the lung sound of the patient obtained by the stethoscope may be mixed with noise transmitted from the inside of the body, irrespective of the patient's health condition, which may make it difficult to check the actual health condition of the patient.

That is, in the digital stethoscopy system according to the prior art, since the transmission unit performs various functions, such as amplification of the sound signal of the cardiac sound or the lung sound, removal of noise, separation of frequency, transmission and reception of data using wireless communication, and the like, the configuration of the transmission unit becomes complicated for a fine filtering processing and a high-speed arithmetic processing such as FFT (fast Fourier transform), and the manufacturing cost thereof increases.

In addition, the conventional digital stethoscopy system cannot separate and output the cardiac sound and the lung sound, even when the cardiac sound and the lung sound are required to be obtained separately in some cases.

SUMMARY OF THE INVENTION

In order to solve the above problems, an aspect of the present invention provides a multi-channel digital stethoscopy system for separating and filtering stethoscopy sounds received from a plurality of transmission units by frequency in a single reception terminal, dividing the filtered stethoscopy sounds into cardiac sounds and lung sounds, and then outputting the same.

In view of the foregoing, an embodiment of the present embodiment may provide a multi-channel digital stethoscopy system including: a plurality of transmission units configured to receive and amplify stethoscopy signals from a patient, convert the amplified stethoscopy signals into digital signals, and output the digital signals together with predetermined unique ID information; and a reception terminal configured to receive the stethoscopy signals and the unique ID information output from the plurality of transmission units, classify the stethoscopy signals by the unique ID information, separate the classified stethoscopy signals by frequency to extract cardiac sounds, lung sounds, and noise, convert the extracted cardiac sounds and lung sounds into sound signals, and output the sound signals as the stethoscopy signals of the transmission units according to the unique ID information.

In addition, the transmission unit according to the embodiment may include: a sound input unit for detecting a stethoscopy signal including a vibration signal and a sound signal transmitted from the patient; an amplifier for amplifying the detected stethoscopy signal; an ADC for converting the amplified stethoscopy signal into a digital signal; and a wireless communication unit for transmitting the digital signal converted from the stethoscopy signal using a predetermined wireless communication format.

In addition, the transmission unit according to the embodiment may further include an attachment unit to be attached and fixed to a body of the patient.

In addition, the reception terminal according to the embodiment may include: an input unit for inputting setting signals of the transmission units and an operation control signal of the reception terminal; a wireless communication unit for transmitting the setting signals to the transmission units and receiving the stethoscopy signals and the unique ID information output from the transmission units; a filter for separating the received stethoscopy signals by frequency to remove noise except the cardiac sounds and the lung sounds; a controller for performing control so as to convert the cardiac sounds and the lung sounds into sound signals, match the sound signals with the unique ID information of the transmission units, and output the stethoscopy signals for the respective transmission units; and a sound output unit for outputting sound signals corresponding to the stethoscopy signals output from the controller.

In addition, the reception terminal according to the embodiment may further include a display unit for displaying frequency signals of the cardiac sounds and the lung sounds output from the respective transmission units and an operation state of the reception terminal.

In addition, the reception terminal according to the embodiment may further include a storage unit for storing position information set for each transmission unit, and sound signals and frequency signals of the cardiac sounds and the lung sounds output from the respective transmission units.

The present invention can provide accurate and detailed medical examination information by separating and filtering stethoscopy sounds received from a plurality of transmission units by frequency in a single reception terminal, dividing the filtered stethoscopy sounds into cardiac sounds and lung sounds, and then outputting the same.

In addition, the present invention is able to reduce the manufacturing cost by simplifying the configuration of the transmission unit.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION OF THE EXEMPLARY EMBODIMENTS

Hereinafter, a preferred embodiment of a multi-channel digital stethoscopy system according to an embodiment of the present invention will be described in detail with reference to the accompanying drawings.

Before describing the specific details for the embodiments of the present invention, it should be noted that configurations that are not directly related to the technical concept of the present invention have been omitted without obscuring the technical concept of the present invention.

In addition, the terms or words used in the present specification and claims should be interpreted so as to comply with the technical spirit of the invention, based on the principle that the inventor can define an appropriate meaning of a term in order to explain the invention in best ways.

The expression "one element 'includes' a component" means that the element may further include other components, instead of excluding the same.

In addition, the term "unit", "~er (or)", "module", or the like indicates a unit that processes at least one function or operation, which may be divided into hardware, software, or a combination thereof.

In addition, the term "at least one" is defined as including a single piece and a plurality of pieces, and it will be obvious that even if a component is expressed without "at least one", it may encompass a single component or a plurality of components so that a single component or a plurality of components may be provided.

In addition, a single component or a plurality of components may be provided according to the embodiment.

Figure 1:
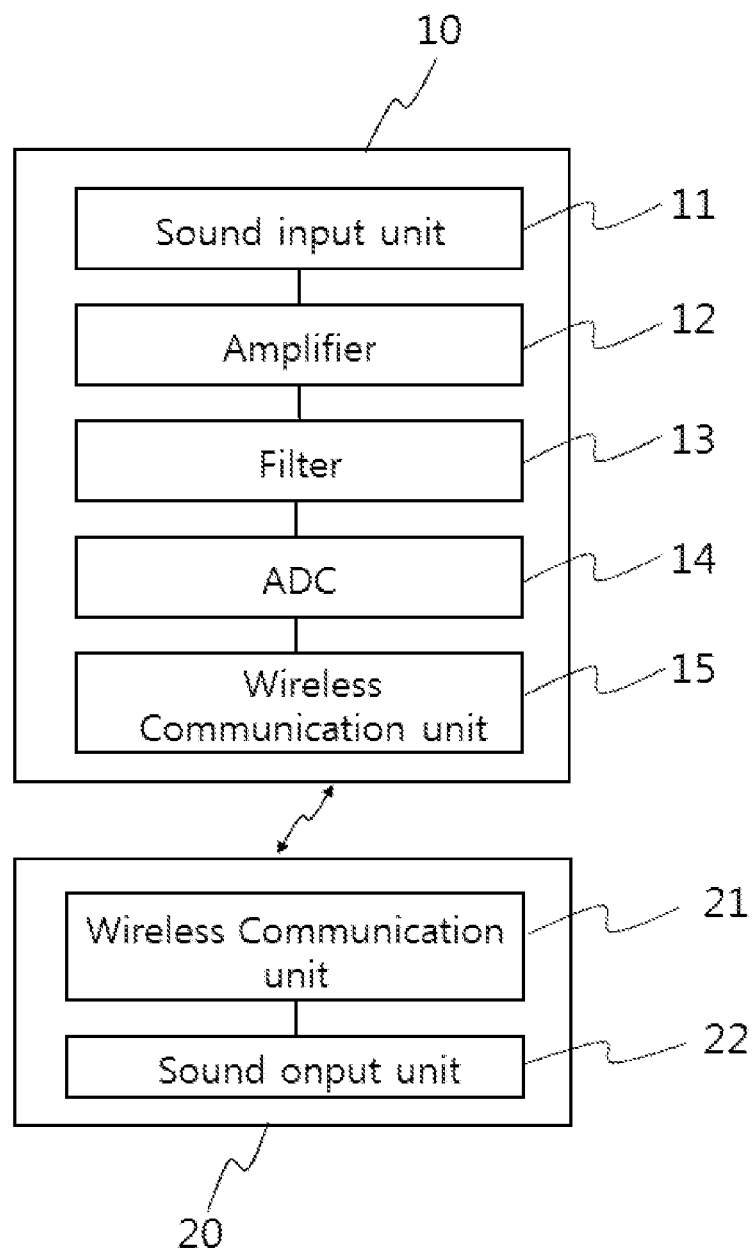
FIG. 1 is a block diagram illustrating a digital stethoscopy system according to the prior art.
Figure 2:
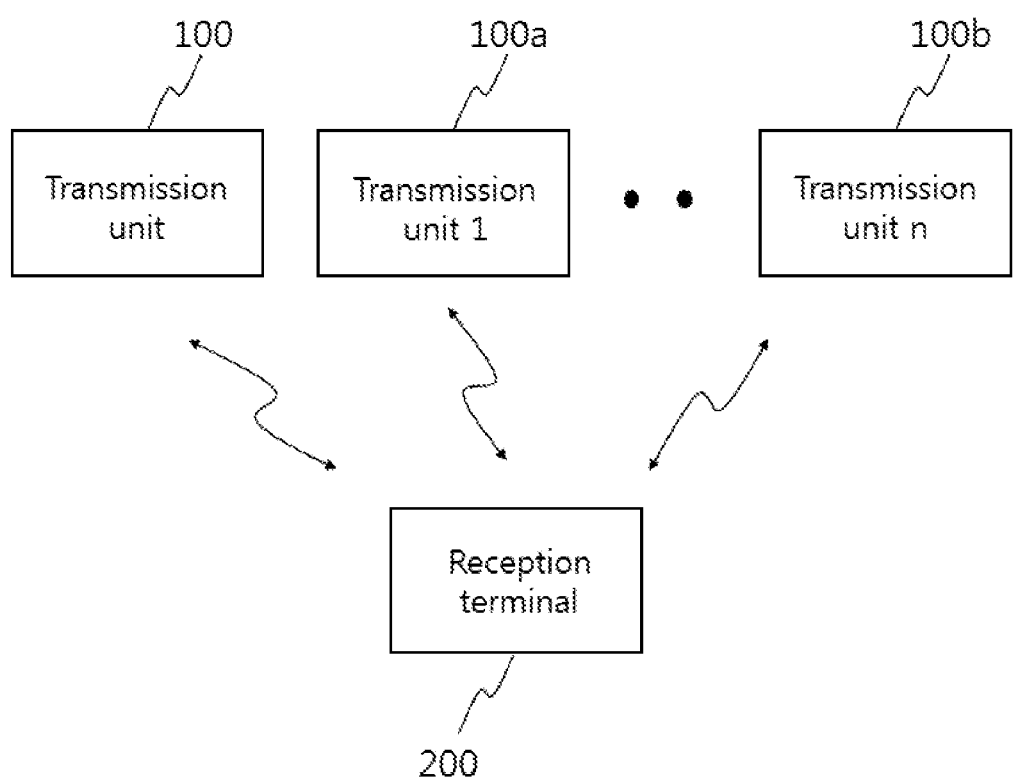
FIG. 2 is a block diagram illustrating the configuration of a multi-channel digital stethoscopy system according to an embodiment of the present invention.
Figure 3:
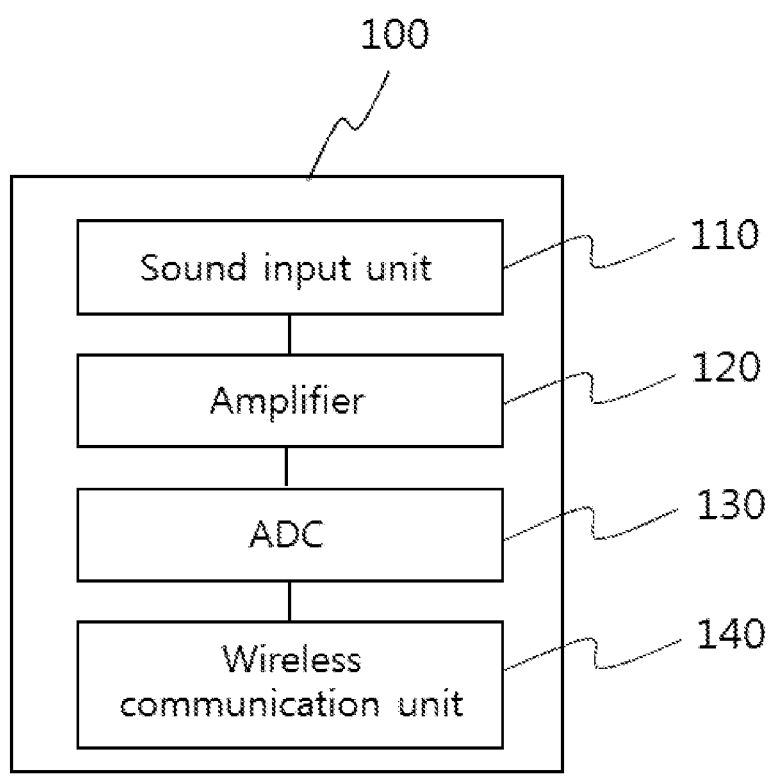
FIG. 3 is a block diagram illustrating the configuration of a transmission unit according to the embodiment in FIG. 2.

FIG. 2 is a block diagram illustrating the configuration of a multi-channel digital stethoscopy system according to an embodiment of the present invention. FIG. 3 is a block diagram illustrating the configuration of a transmission unit according to the embodiment in FIG. 2, and FIG. 4 is a block diagram illustrating the configuration of a reception terminal according to the embodiment in FIG. 2.

Figure 4:
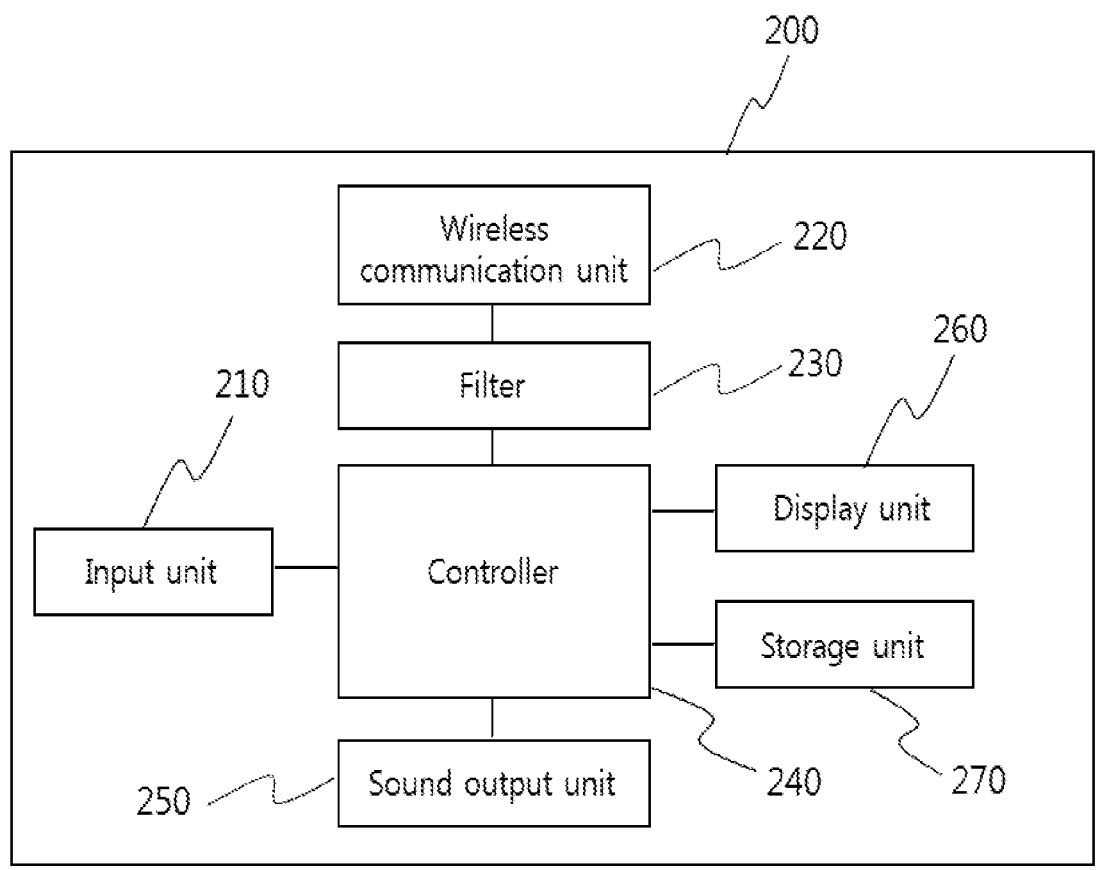
FIG. 4 is a block diagram illustrating the configuration of a reception terminal according to the embodiment in FIG. 2.

As shown in FIGS. 2 to 4, a multi-channel digital stethoscopy system according to an embodiment of the present invention is configured to include a plurality of transmission units 100, 100a, and 100b attached to the body of a patient to detect stethoscopy signals and a reception terminal 200 for receiving stethoscopy signals from the plurality of transmission units 100, 100a, and 100b to output cardiac sounds and lung sounds.

The transmission units 100, 100a, and 100b are configured to receive and output stethoscopy signals from the patient, and may be attached to various positions of the body such as a chest of the patient, a back of the patient, or the like in order to detect the stethoscopy signals.

In addition, the transmission units 100, 100a, and 100b may be configured to include a sound input unit 110 that operates independently for each transmission unit and receives a stethoscopy signal generated from the patient.

The sound input unit 110 may be configured to detect a stethoscopy signal including a vibration signal and a sound signal transmitted from the patient, and may include a vibration sensing device for detecting and outputting a vibration signal transmitted through the skin of the patients body and a sound collecting device for collecting a sound signal generated inside the patients body, such as a microphone.

In addition, the transmission unit 100, 100a, or 100b may be configured to include an amplifier 120 for amplifying the stethoscopy signal including a vibration signal and a sound signal, which is collected through the sound input unit 110.

In addition, the transmission unit 100, 100a, or 100b may be configured to include an ADC 130 for converting the stethoscopy signal amplified by the amplifier 120 into a digital signal.

In addition, the transmission unit 100, 100a, or 100b may be configured to include a wireless communication unit 140 for transmitting a digital signal converted from the stethoscopy signal to the reception terminal 200 using a short-range wireless communication format, such as Bluetooth, Zigbee, NFC, or the like.

In addition, the transmission unit 100, 100a, or 100b may transmit, to the reception terminal 200, the stethoscopy signal together with predetermined unique ID information of the transmission unit.

The unique ID information may be set by a user in a process of connecting to the reception terminal 200.

In addition, the transmission unit 100, 100a, or 100b may be configured to further include an attachment unit to be attached and fixed to the patient's body in the form of a patch.

The reception terminal 200 may be configured to receive stethoscopy signals and unique ID information output from a plurality of transmission units 100, 100a, and 100b and output sound signals corresponding to cardiac sounds and lung sounds, and may include an input unit 210, a wireless communication unit 220, a filter 230, a controller 240, a sound output unit 250, a display unit 260, and a storage unit 270.

In addition, the reception terminal 200 may be a server or a computer capable of accessing the server.

Here, the computer may include, for example, a navigation system, and a notebook PC, a desktop PC, a laptop PC, and the like equipped with a web browser.

In addition, the reception terminal 200 may include all kinds of handheld-based wireless communication devices such as mobile terminals capable of installation of application programs, terminals of PCS (Personal Communication System), GSM (Global System for Mobile Communications), PDC (Personal Digital Cellular), PHS (Personal Handyphone System), PDA (Personal Digital Assistant), IMT (International Mobile Telecommunication)-2000, CDMA (Code Division Multiple Access)-2000, W-CDMA (W-Code Division Multiple Access), and Wibro (Wireless Broadband Internet), smart phones, smart pads, tablet PCs, and the like.

The input unit 210 may be configured to receive setting signals of the transmission units 100, 100a, and 100b, which are input from the user, information on the installation position of the transmission unit 100, 100a, or 100b, a setting value or range of the stethoscopy signal to be detected from the patient, and an operation control signal of the reception terminal 200 including volume of the sound output unit 250 and the like, and may include a keypad, a button switch, a jog shuttle switch, a touch screen, and the like.

The wireless communication unit 220 transmits a signal set through the input unit 210 to the transmission units 100, 100a, and 100b and receives stethoscopy signals and unique ID information output from the transmission units 100, 100a, and 100b.

The filter 230 may be configured to separate the received stethoscopy signals by frequency, thereby removing noise except cardiac sounds and lung sounds, and may include a high-pass filter for filtering a high frequency component and a low-pass filter for filtering a low frequency component.

In addition, the filter 230 may further include a digital attenuator for reducing the amplitude of a digital signal to a predetermined value or less.

In addition, the filter 230 may be configured to have a high-pass filter and a low-pass filter, and the high-pass filter and the low-pass filter are combined to separate the cardiac sounds and the lung sounds transmitted from the patient's body.

For example, the cardiac sound of the patient may correspond to a digital signal in a lower sound range than the lung sound, and the lung sound of the patient may correspond to a digital signal in a higher sound range than the cardiac sound.

That is, the frequency range of a generated sound may differ between the body parts corresponding to the cardiac sound and the lung sound. Specifically, the cardiac sound has a frequency of 20 to 200 Hz, the lung sound has a frequency of 100 to 500 Hz, and other internal organ sounds have a frequency of 50 to 500 Hz.

Therefore, the filter 230 is configured as a combination of a high-pass filter and a low-pass filter according to the body part to be auscultated, thereby separating the cardiac sound and the lung sound of the patient corresponding to the stethoscopy signals in different sound ranges.

In addition, the filter 230 separates the stethoscopy signal into a cardiac sound and a lung sound for extraction according to frequency and eliminates other signals by classifying the same as noise.

The controller 240 may classify the stethoscopy signals for the respective transmission units 100, 100a, and 100b using the unique ID information transmitted together with the stethoscopy signals received from the transmission units 100, 100a, and 100b.

That is, the controller 240 matches the cardiac sounds and the lung sounds separated through the filter 230 with the unique ID information of the transmission units 100, 100a, and 100b.

In addition, the controller 240 stores the matched result, and sound signals and frequency signals of the cardiac sounds and the lung sounds output from respective transmission units 100, 100a, and 100b in the storage unit 270.

In addition, the controller 240 may perform control so as to convert the separated cardiac sounds and lung sounds into sound signals for the respective transmission units 100, 100a, and 100b and output the same.

In addition, the controller 240 may perform control so as to convert the separated cardiac sounds and lung sounds into waveform signals according to frequency for the respective transmission units 100, 100a, and 100b and output the same.

In addition, the controller 240 may analyze the cardiac sounds and the lung sounds through a fine filtering processing and a high-speed operation process such as FFT (fast Fourier transform).

The sound output unit 250 is configured to output a sound signal output from the controller 240, and may include at least one sound output device such as a speaker or earphones.

That is, the sound output unit 250 may be configured as a single sound output device, or may be configured as a plurality of speakers to output the cardiac sounds and the lung sounds, respectively, in response to the sound signals output from the respective transmission units 100, 100a, and 100b.

The display unit 260 is configured to output the waveform signal for each frequency, which is output from the controller 240, for each transmission unit 100, 100a, or 100b, thereby displaying frequency signals of the cardiac sounds and the lung sounds.

In addition, the display unit 260 may display an operation state of the reception terminal 200, and may be configured as a display device such as an LCD or an LED.

The storage unit 270 stores position information set by the user for the respective transmission units 100, 100a, and 100b through the input unit 210, and sound signals and frequency-waveform signals of the cardiac sounds and the lung sounds output from the respective transmission units 100, 100a, and 100b.

Accordingly, the present invention can provide accurate and detailed medical examination by separating and filtering stethoscopy signals received from a plurality of transmission units by frequency in a single reception terminal, dividing the filtered stethoscopy sounds into cardiac sounds and lung sounds, and then outputting the same.

As described above, although the present invention has been described with reference to a preferred embodiment, those skilled in the art may understand that the present invention may be variously modified and changed without departing from the spirit and scope of the invention claimed in the claims below.

In addition, the thicknesses of the lines or the sizes of the components shown in the drawings for the explanation of the embodiment may be exaggerated for clarity and convenience of the description. The terms described above are defined in consideration of functions in the present invention, and may vary according to the intention or practices of a user or operator, so that the terms should be construed on the basis of the content throughout the specification.

DRAWING LEGEND INSERTION

11: Sound input unit
12: Amplifier
13: Filter
15: Wireless communication unit
21: Wireless communication unit
22: Sound output unit
100: Transmission unit
100a: Transmission unit 1
100b: Transmission unit n
110: Sound input unit
120: Amplifier
140: Wireless communication unit
200: Reception terminal
210: Input unit
220: Wireless communication unit
230: Filter
240: Controller
250: Sound output unit
260: Display unit
270: Storage unit

What is claimed is:

1. A multi-channel digital stethoscopy system comprising:
a plurality of transmission units configured to receive and amplify stethoscopy signals from a patient, convert the amplified stethoscopy signals into digital signals, and output the digital signals together with predetermined unique ID information; and
a reception terminal configured to receive the stethoscopy signals and the unique ID information output from the plurality of transmission units, classify the stethoscopy signals by the unique ID information, separate the classified stethoscopy signals by frequency to extract cardiac sounds, lung sounds, and noise, convert the extracted cardiac sounds and lung sounds into sound signals, and output the sound signals as the stethoscopy signals of the transmission units according to the unique ID information.

2. The multi-channel digital stethoscopy system of claim 1, wherein the plurality of transmission units comprise:
a sound input unit for detecting a stethoscopy signal including a vibration signal and a sound signal transmitted from the patient;
an amplifier for amplifying the detected stethoscopy signal;
an ADC for converting the amplified stethoscopy signal into a digital signal; and
a wireless communication unit for transmitting the digital signal converted from the stethoscopy signal using a predetermined wireless communication format.

3. The multi-channel digital stethoscopy system of claim 2, wherein the plurality of transmission units further comprise an attachment unit to be attached and fixed to a body of the patient.

4. The multi-channel digital stethoscopy system of claim 1, wherein the reception terminal comprises:
an input unit for inputting setting signals of the transmission units and an operation control signal of the reception terminal;
a wireless communication unit for transmitting the setting signals to the transmission units and receiving the stethoscopy signals and the unique ID information output from the transmission units;
a filter for separating the received stethoscopy signals by frequency to remove noise except the cardiac sounds and the lung sounds;
a controller for performing control so as to convert the cardiac sounds and the lung sounds into sound signals, match the sound signals with the unique ID information of the transmission units, and output the stethoscopy signals for the respective transmission units; and
a sound output unit for outputting sound signals corresponding to the stethoscopy signals output from the controller.

5. The multi-channel digital stethoscopy system of claim 4, wherein the reception terminal further comprises a display unit for displaying frequency signals of the cardiac sounds and the lung sounds output from the respective transmission units and an operation state of the reception terminal.

6. The multi-channel digital stethoscopy system of claim 5, wherein the reception terminal further comprises a storage unit for storing position information set for each transmission unit, and sound signals and frequency signals of the cardiac sounds and the lung sounds output from the respective transmission units.

* * * * *